(12) United States Patent
Marko et al.

(10) Patent No.: US 6,803,440 B2
(45) Date of Patent: Oct. 12, 2004

(54) CATALYSTS FOR HYDROSILYLATION REACTIONS

(75) Inventors: Istvan Marko, Grez-Doiceau (BG); Sebastien Sterin, Lyons (FR)

(73) Assignee: Rhodia Chimie, Courbevoie (FR)

( * ) Notice: Subject to any disclaimer, the term of this patent is extended or adjusted under 35 U.S.C. 154(b) by 0 days.

(21) Appl. No.: 10/149,014

(22) PCT Filed: Dec. 1, 2000

(86) PCT No.: PCT/FR00/03362

§ 371 (c)(1),
(2), (4) Date: Sep. 13, 2002

(87) PCT Pub. No.: WO01/42258

PCT Pub. Date: Jun. 14, 2001

(65) Prior Publication Data

US 2003/0083454 A1 May 1, 2003

(30) Foreign Application Priority Data

Dec. 7, 1999 (FR) .............................. 99 15432

(51) Int. Cl.[7] .............................. C08G 77/08
(52) U.S. Cl. .............................. 528/14; 528/15; 528/21; 528/32; 528/31; 502/325
(58) Field of Search .............................. 528/15, 14, 21, 528/32, 31; 502/325

(56) References Cited

FOREIGN PATENT DOCUMENTS

FR 2 474 890 8/1981

OTHER PUBLICATIONS

Chemical Abstracts, vol. 129, No. 17, Oct. 26, 1998, Abstract No. 216758; Enders et al. XP002143369 Abstract & Eur. J. Inorg. Chem (1998), vol. 7, pp. 913–919, 1998.

*Primary Examiner*—Kuo-Liang Peng
(74) *Attorney, Agent, or Firm*—Burns, Doane, Swecker & Mathis, L.L.P.

(57) ABSTRACT

The invention relates to metal complexes of formula (I)

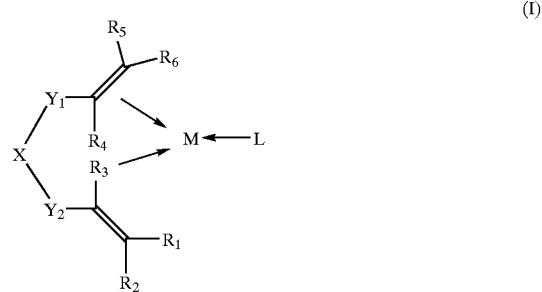

These complexes are particularly suitable for use as catalysts of hydrosilylation reactions.

16 Claims, No Drawings

CATALYSTS FOR HYDROSILYLATION REACTIONS

The invention relates to a catalyst which is appropriate for catalyzing hydrosilylation reactions.

The addition of an organosilylated compound having an Si—H unit to an olefin or to an acetylene derivative through the formation of a carbon-silicon bond (hydrosilylation reaction) is conventionally carried out in the presence of a metal catalyst. The hydrosilylation reaction is schematically represented in the following manner in the case of olefins:

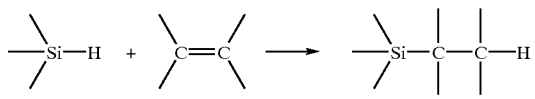

As an example of a catalyst, platinum catalysts have been recommended by numerous authors. Thus, U.S. Pat. No. 2,823,218 describes a chloroplatinic acid as catalyst. U.S. Pat. No. 2,970,150 proposes the use of metallic platinum on a finely divided support. The hydrosilylation methods described in these patents are however, not very attractive from an economic point of view since they require the use of large quantities of platinum catalyst.

Thus, up until now, most industrial hydrosilylation reactions are catalyzed by the Karstedt solution which consists of complexes of platinum having the oxidation number 0. The general formula of the Karstedt complex is $Pt_2$ (tetramethyldivinylsiloxane)$_3$:

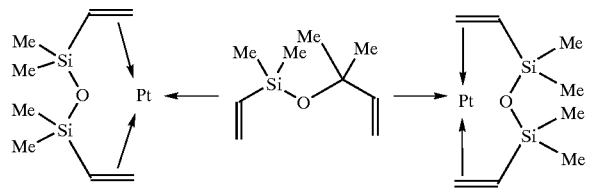

where Me represents methyl.

One of the disadvantages of this catalyst lies in the possible instability of the catalyst during the course of a reaction: it has been possible to observe the precipitation of metallic platinum and the formation of insoluble colloids in the reaction medium: this instability of the catalyst in the reaction medium has the effect of reducing the catalytic activity. Furthermore, it results in cloudy and highly colored solutions which are not much liked by the user since they lead to the formation of highly colored hydrosilylation products.

Another major disadvantage of the Karstedt catalyst is the concomitant formation of by-products of the hydrosilylation reaction: alongside the hydrosilylation products, the products resulting from olefin double bond isomerization reactions and/or hydrogenation reactions are isolated.

One of the objectives of the present invention is therefore to provide a stable catalyst complex which makes it possible to limit the side reactions.

Because of its excellent stability, the complex of the invention moreover makes it possible to operate at higher reaction temperatures.

The other advantages of the invention will appear to a person skilled in the art on reading the preferred embodiments of the invention.

The invention relates more particularly to a metal complex of formula I:

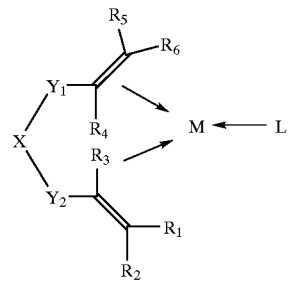

in which:

M represents a metal having an oxidation number 0 chosen from the group 8 metals in the Periodic Table as published in the Handbook of Chemistry and Physics, 65th edition, 1984–1985;

X represents O, $NR_a$ or $CR_fR_g$;

$Y_1$ and $Y_2$ represent, independently of each other, $CR_bR_c$ or $SiR_dR_e$;

$R_1$, $R_2$, $R_5$ and $R_6$, which are identical or different, are chosen from a hydrogen atom, an alkyl group and an aryl group optionally substituted with alkyl;

$R_3$, $R_4$, $R_a$, $R_b$, $R_c$, are independently chosen from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_d$ and $R_e$ are independently chosen from alkenyl; alkynyl; alkyl; alkoxy; acyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two $R_d$ groups linked to two separate silicon atoms together form a chain of formula:

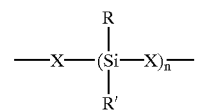

in which n is an integer from 1 to 3; X is as defined above; R and R', which are identical or different, take any one of the meanings given above for $R_e$, it being understood that when n is 2 or 3, a single silicon atom of said chain may be substituted with one or two alkenyl or alkynyl groups;

or alternatively when $Y_1$ and $Y_2$ independently represent $SiR_dR_e$, two $R_d$ groups linked to separate silicon atoms together form a saturated hydrocarbon chain, the two $R_b$ groups together with said silicon atoms and X forming a 6- to 10-membered ring; or alternatively when $Y_1$ and $Y_2$ independently represent $CR_bR_c$, two $R_b$ groups linked to separate carbon atoms together form a saturated hydrocarbon chain, the two $R_b$ groups together with the carbon atoms carrying them and X form a 6- to 10-membered ring;

$R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_2G_3$ where $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy;

L represents a carbene of formula II.1 or II.2:

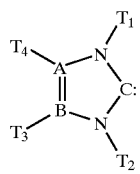

II.1

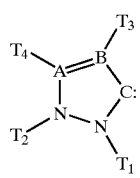

II.2 in which:

A and B independently represent C or N, it being understood that when A represents N, then $T_4$ represents nothing and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy;

$T_1$ and $T_2$ independently represent an alkyl group; an alkyl group which is perfluorinated or optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively the substituents $T_1$, $T_2$, $T_3$ and $T_4$, may form in pairs, when they are located on two adjacent summits in the formulae II.1 and II.2, a saturated or unsaturated hydrocarbon chain.

According to the invention, the oxidation number 0 of the metal M is an essential characteristic of the invention.

Preferably, the group 8 metals which M represents are palladium, platinum or nickel. According to a more preferred embodiment of the invention, M represents platinum having the oxidation number 0.

The expression alkyl is understood to mean, according to the invention, a linear or branched, saturated hydrocarbon chain, preferably having from 1 to 10 carbon atoms, for example from 1 to 8 carbon atoms, even better from 1 to 7 carbon atoms.

Examples of alkyl groups are in particular methyl, ethyl, isopropyl, n-propyl, tert-butyl, isobutyl, n-butyl, n-pentyl, isoamyl and 1,1-dimethylpropyl.

According to the invention, the alkyl portion of the alkoxy radical is as defined above.

The alkyl radical which is perfluorinated or optionally substituted with a perfluoroalkyl group preferably has the formula:

$$—(CH_2)_p—C_qF_{2q+1}$$

in which p represents 0, 1, 2, 3 or 4; q is an integer from 1 to 10; and $C_qF_{2q+1}$ is linear or branched. Preferred examples of this radical are: $—(CH_2)_2—(CF_2)_5—CF_3$ and $—(CF_2)_7—CF_3$.

The expression aryl denotes an aromatic hydrocarbon group having from 6 to 18 carbon atoms, which is monocyclic or polycyclic, and preferably monocyclic or bicyclic. It should be understood that in the context of the invention, the expression polycyclic aromatic radical is understood to mean a radical having two or more aromatic rings, condensed to each other, that is to say having, in pairs, at least two carbons in common. By way of example, there may be mentioned the phenyl, naphthyl, anthryl and phenanthryl radicals.

The expression arylalkyl denotes an alkyl group as defined above, substituted with one or more aryl groups on its hydrocarbon chain, the aryl group being as defined above. Examples thereof are benzyl and triphenylmethyl.

The expression acyl is understood to mean, according to the invention, a group $R_o—CO—$ where $R_o$ represents alkyl as defined above; or alternatively a group $Ar—CO—$ where Ar represents an aryl group as defined above, or alternatively an arylalkyl in which aryl and alkyl are as defined above and in which the aryl portion is optionally substituted with alkyl.

The expression cycloalkyl is understood to mean a mono- or polycyclic, preferably mono- or bicyclic, saturated hydrocarbon radical preferably having from 3 to 10 carbon atoms, even better from 3 to 8. The expression polycyclic saturated hydrocarbon radical is understood to mean a radical having two or more cyclic rings attached to each other by σ bonds and/or condensed in pairs.

Examples of polycyclic cycloalkyl groups are adamantane and norbornane.

Examples of monocyclic cycloalkyl groups are cyclopropyl, cyclobutyl, cyclopentyl, cyclohexyl, cycloheptyl and cyclooctyl.

The expression alkenyl is understood to mean a linear or branched unsaturated hydrocarbon chain having at least one olefin double bond, and more preferably a single double bond. Preferably, the alkenyl group has from 2 to 8 carbon atoms, even better from 2 to 6.

Preferred examples of alkenyl groups are vinyl and allyl groups.

The expression alkynyl is understood to mean, according to the invention, a linear or branched, unsaturated hydrocarbon chain having at least one acetylene triple bond, and more preferably a single triple bond. Preferably, the alkynyl group has from 2 to 8 carbon atoms, even better from 2 to 6 carbon atoms. By way of example, there may be mentioned the acetylenyl group, as well as the propargyl group.

According to a preferred embodiment of the invention, $Y_1$ and $Y_2$ either both represent $CR_bR_c$, or both $SiR_dR_e$, such that the preferred compounds of the invention either have the formula I.1, or the formula I.2:

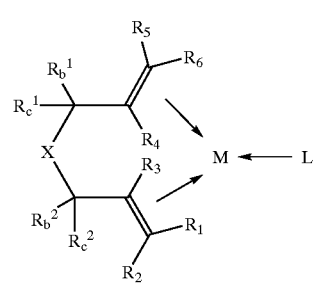

I.1

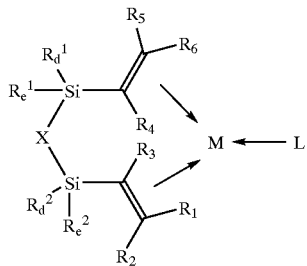

where $R_b^1$ and $R_c^1$ are the substituents $R_b$ and $R_c$ of $Y_1$ in formula I.1;

$R_b^2$ and $R_c^2$ are the substituents $R_b$ and $R_c$ of $Y_2$ in formula I.2;

$R_d^1$ and $R_e^1$ are the substituents $R_d$ and $R_e$ of $Y_1$ in formula I.1;

$R_d^2$ and $R_e^2$ are the substituents $R_d$ and $R_e$ of $Y_2$ in formula I.2.

Thus, $R_b^1$ may be identical to or different from $R_b^2$; $R_c^1$ may be identical to or different from $R_c^2$; $R_d^1$ may be identical to or different from $R_d^2$; and $R_e^1$ may be identical to or different from $R_e^2$.

Preferably, $R_b^1=R_b^2$; $R_c^1=R_c^2$; $R_d^1=R_d^2$; and $R_e^1=R_e^2$.

Among the latter compounds those for which $R_3=R_4$; $R_5=R_2$; and $R_1=R_6$ are further preferred.

According to another preferred variant of the invention, $R_d^1$ and $R_d^2$ together form:

(a) either a chain

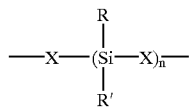

in which n is an integer from 1 to 3; X is as defined above; and R and R', which are identical or different, take any one of the meanings given above for $R_e$, it being understood that when n is 2 or 3, a single silicon atom of said chain may be substituted with one or two alkenyl or alkynyl groups;

(b) or a saturated hydrocarbon chain such that the two substituents $R_d$, together with the two silicon atoms carrying them and X, form a 6- to 10-membered, preferably 6- to 8-membered, ring.

When $R_d^1$ and $R_d^2$ form the chain (a), it is preferable for n to be equal to 1 or 2 (even better n is equal to 1) and that $R=R_e$, the two groups $R_e$ carried by the two silicon atoms being identical. In this case, $R_e$ preferably represents alkyl, for example methyl. Even better, in these compounds, R' represents —$CR_3$=$CR_1R_2$ and $R_1=R_6$; $R_5=R_2$; and $R_3=R_4$.

When $R_d^1$ and $R_d^2$ form the chain (b), it is preferable for the two groups $R_d$, together with the two silicon atoms and the group X, to form an 8-membered ring. In this case, it is preferable that $R_e^1$ is identical to $R_e^2$. These compounds have the general formula:

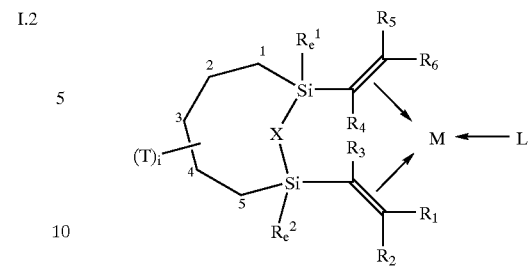

where T represents alkyl, i is an integer between 0 and 5, T being located on one or more of the summits 1, 2, 3, 4 and 5 of the above formula.

In the same manner, when $Y_1$ and $Y_2$ represent $CR_bR_c$, the two groups $R_b$ linked to separate carbon atoms may together form a saturated hydrocarbon chain (c) such that the two groups $R_b$ together with the carbons carrying them and X form a 6- to 10-membered ring. Preferably, the ring formed is an 8-membered ring, in which case the metal complex corresponds to the formula:

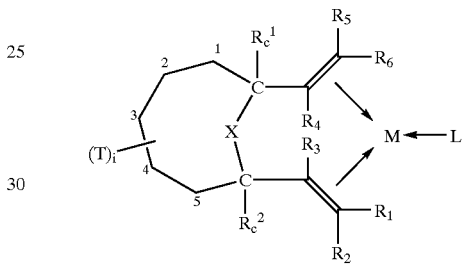

where T represents alkyl; i is an integer between 0 and 5, T being located on one or more of the summits 1, 2, 3, 4 and 5 of the formula above.

In the context of the invention, two groups $R_d$ linked to two separate silicon atoms may form a chain of formula:

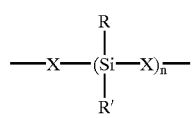

When this is the case, it is preferable that X represents O in the compounds of the invention. These preferred compounds have the general formula:

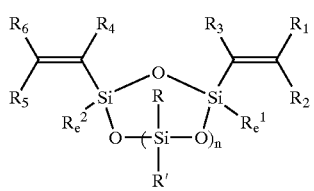

Among these compounds, it is preferable that $R_e^1=R_e^2$. Advantageously $R_e^1=R_e^2$ represents alkyl (for example methyl).

Preferably, n is equal to 1 or 2 and $R=R_e^1$, it being understood that when n is equal to 2, a single silicon atom of the chain O—(SiRR'—O)$_n$ may be substituted with one or two alkenyl or alkynyl groups. Even better, R'=—$CR_3$=$CR_1R_2$ and $R_1=R_6$; $R_2=R_5$ and $R_3=R_4$.

The expression "represents nothing" means that the substituents —$T_3$, respectively —$T_4$, are nonexistent. Indeed, in the formulae II.1 and II.2, the nitrogen atom is trivalent, such that when A or B represents N, the nitrogen atom cannot have an additional substituent.

According to a particular embodiment of the invention, the carbenes of formulae II.1 and II.2 have at least two condensed rings, that is to say that at least two substituents among $T_1$, $T_2$, $T_3$ and $T_4$, situated on two adjacent summits, together form a saturated or unsaturated hydrocarbon chain preferably having from 3 to 6 carbon atoms. The expression saturated or unsaturated hydrocarbon chain is understood to mean a linear or branched hydrocarbon chain which may or may not have one or more unsaturations of the olefin double bond or acetylene triple bond type.

When the carbenes II.1 and II.2 have two condensed rings, they therefore correspond to one of the following formulae, in which (alk) represents a saturated or unsaturated hydrocarbon chain:

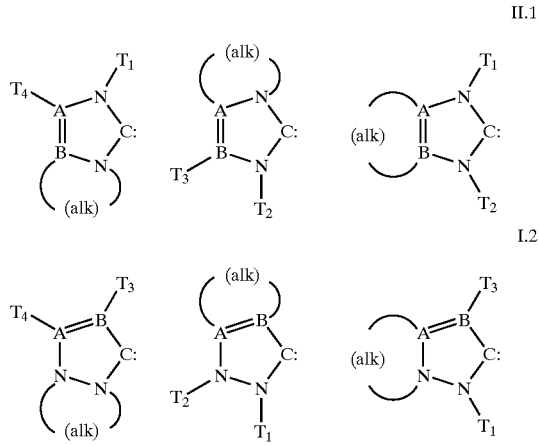

It should be understood however that the carbenes II.1 and II.2 may have more than two condensed rings.

When $R_f$ and/or $R_g$ represents $SiG_1G_2G_3$, it is preferable that $R_f$ and/or $R_g$ are trialkylsilyl, for example $SiG_1G_2G_3$ where $G_1=G_2=G_3=$alkyl.

Subgroups of the metal complexes of the invention consist of the complexes for which:

X=O; $Y_1$ and $Y_2$ independently represent $SiR_dR_e$; or
X=$NR_a$; $Y_1$ and $Y_2$ independently represent $CR_bR_c$; or
X=$NR_a$; $Y_1$ and $Y_2$ independently represent $SiR_dR_e$; or
X=$CR_fR_g$; $Y_1$ and $Y_2$ independently represent $CR_bR_c$; or
X=$CR_fR_g$; $Y_1$ and $Y_2$ independently represent $SiR_dR_e$.

Among these metal complexes of formula I, there are preferred those for which:

when X represents O, $Y_1$ and $Y_2$ independently represent $SiR_dR_e$; or
when X represents $NR_a$, $Y_1$ and $Y_2$ independently represent $CR_bR_c$; or
when X represents $CR_fR_g$, $Y_1$ and $Y_2$ independently represent $CR_bR_c$.

Most preferably, X represents O and $Y_1$ and $Y_2$ independently represent $SiR_dR_e$ in the metal complex of formula I. In the context of the invention, the expression "independently represent" means that the substituents designated are either identical or different.

Still preferably, $R_1$, $R_2$, $R_5$ and $R_6$ are hydrogen atoms.

Preferred meanings of $R_3$ and $R_4$ are in particular a hydrogen atom; an alkyl group; an aryl group optionally substituted with alkyl; and a cycloalkyl group optionally substituted with alkyl. Among these preferred meanings, it is particularly advantageous that $R_3$ and $R_4$, which are identical, represent a hydrogen atom; ($C_3$–$C_8$)cycloalkyl or ($C_1$–$C_8$)alkyl.

Still preferably, the diolefin ligand of the complex of formula I is symmetric, that is to say that $R_5=R_2$; $R_6=R_1$; $R_3=R_4$ and the two groups $Y_1$, $Y_2$ are strictly identical to each other, that is $Y_1=CR_b^1R_c$ and $Y_2=CR_b^2R_c$ where $R_b^1$ and $R_b^2$ together form a symmetric chain, or alternatively $Y_1=SiR_d^1R_e$ and $Y_2=SiR_d^2R_e$ where $R_d^1$ and $R_d^2$ together form a symmetric chain.

A preferred group of complexes according to the invention consists of the complexes of formula I in which L represents a carbene of formula II.1.

Preferably, A and B in the formulae II.1 and II.2 both represent a carbon atom.

Preferred meanings of $T_1$ and $T_2$ are alkyl; cycloalkyl; arylalkyl; and aryl which is optionally substituted with alkyl.

Preferred meanings of $T_3$ and $T_4$ are hydrogen; alkyl; cycloalkyl; arylalkyl; and aryl which is optionally substituted with alkyl.

Preferably, when $T_1$, $T_2$, $T_3$ or $T_4$ represents alkyl, then alkyl is methyl, isopropyl or tert-butyl.

Likewise, when $T_1$, $T_2$, $T_3$ or $T_4$ represents aryl, then aryl is phenyl.

When $T_1$, $T_2$, $T_3$ or $T_4$ represents aryl optionally substituted with alkyl, then $T_1$, $T_2$, $T_3$ or $T_4$ is tolyl or xylyl.

When $T_1$, $T_2$, $T_3$ or $T_4$ represents arylalkyl, then arylalkyl is preferably benzyl or triphenylmethyl.

When $T_1$, $T_2$, $T_3$ or $T_4$ represents cycloalkyl, then cycloalkyl is preferably cyclopentyl, cyclohexyl or adamantyl.

A preferred group of complexes of formula I consists of the complexes for which in the carbene of formulae II.1 or II.2, $T_3$ and $T_4$ represent a hydrogen atom.

Likewise, the complexes of formula I in which $T_1$ and $T_2$ are chosen from ($C_1$–$C_8$)alkyl and ($C_3$–$C_8$)-cycloalkyl form a preferred subgroup. Even better, $T_1$ and $T_2$ are identical and represent ($C_3$–$C_8$)cycloalkyl.

Advantageously, $T_1$ and $T_2$, which are identical or different, represent ($C_1$–$C_8$)alkyl or ($C_3$–$C_8$)-cycloalkyl; or alternatively $R_3$ and $R_4$, which are identical or different, represent ($C_1$–$C_8$)alkyl or ($C_3$–$C_8$)cycloalkyl; or still alternatively $T_1$, $T_2$, $R_3$ and $R_4$, which are identical or different, represent ($C_1$–$C_8$)alkyl or ($C_3$–$C_8$)cycloalkyl.

A particularly preferred group of metal complexes of formula I consists of the complexes of formula:

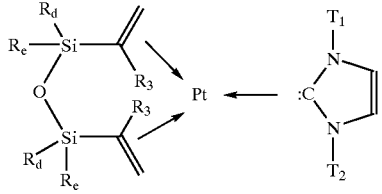

in which:

$R_3$ represents a hydrogen atom; a ($C_1$–$C_8$)alkyl group; or a ($C_3$–$C_8$)cycloalkyl group optionally substituted with ($C_1$–$C_4$)alkyl;

$T_1$ and $T_2$ are identical and represent ($C_1$–$C_8$)alkyl or ($C_3$–$C_8$)cycloalkyl;

$R_d$ and $R_e$ are as defined above.

Other preferred subgroups of the invention are defined as follows:

Metal complexes of formula I in which $Y_1$ and $Y_2$, which are identical, represent $SiR_dR_e$; $R_1=R_2=R_3=R_4=R_5=$ $R_6$=H; X=O; $R_d$ and $R_e$ are independently chosen from alkyl; aryl optionally substituted with alkyl; alkenyl; and alkynyl.

Metal complexes of formula I in which $Y_1$ and $Y_2$, which are identical, represent $SiR_dR_e$; X=O; $R_1$=$R_6$; $R_2$=$R_5$; $R_3$=$R_4$; $R_1$ and $R_2$ independently represent alkyl; $R_3$ represents alkyl or aryl optionally substituted with alkyl; $R_d$ and $R_e$ independently represent alkyl; alkenyl; alkynyl; or aryl optionally substituted with alkyl.

Metal complexes of formula I in which $Y_1$ and $Y_2$, which are identical, represent $SiR_dR_e$; X=O; $R_1$=$R_2$=$R_3$=$R_4$=$R_5$=$R_6$=H; and $R_d$=$R_e$=methyl or alternatively $R_d$=methyl and $R_e$=phenyl.

Metal complexes of formula I in which $Y_1$ and $Y_2$, which are identical, represent $SiR_dR_e$; X=O; $R_1$=$R_3$=$R_4$=$R_6$=H; $R_2$=$R_5$=alkyl.

Metal complexes of formula I in which $Y_1$ and $Y_2$, which are identical, represent $SiR_dR_e$; X=$CR_fR_g$; $R_f$=$R_g$=a hydrogen atom; $R_d$ and $R_e$, which are identical or different, are chosen from alkyl; and aryl optionally substituted with alkyl; $R_1$=$R_6$; $R_2$=$R_5$; $R_3$=$R_4$; $R_1$ and $R_2$ are chosen from a hydrogen atom and an alkyl group; $R_3$ represents a hydrogen atom, alkyl or aryl optionally substituted with alkyl.

Metal complexes of formula I in which $Y_1$ and $Y_2$, which are identical, represent $SiR_dR_e$; X=$CR_fR_g$ where $R_f$ and $R_g$ represent a halogen atom, preferably a chlorine atom or a bromine atom; $R_d$=$R_e$=alkyl, preferably methyl; $R_1$=$R_2$=$R_3$=$R_4$=$R_5$=$R_6$=H.

Metal complexes of formula I in which $Y_1$ and $Y_2$, which are identical, represent $SiR_dR_e$; X=$CR_fR_g$ where $R_f$ and $R_g$ represent $SiG_1G_2G_3$ such as trialkylsilyl (for example $Si(CH_3)_3$); $R_d$=$R_e$=alkyl, preferably methyl; $R_1$=$R_2$=$R_3$=$R_4$=$R_5$=$R_6$=H.

Metal complexes of formula I in which X represents —$NR_a$; $Y_1$ and $Y_2$, which are identical, represent $SiR_dR_e$; $R_1$=$R_6$; $R_2$=$R_5$; $R_3$=$R_4$.

Metal complexes of formula I in which X represents —$NR_a$; $Y_1$=$Y_2$=$SiR_dR_e$; the two groups $R_d$ together form the chain —$NR_a$—$(SiR_eR_d^0—NR_a)_n$— in which $R_d^0$ represents —$CR_3$=$CR_1R_2$; n represents from 1 to 3; $R_1$=$R_6$; $R_2$=$R_5$; and $R_3$=$R_4$.

The complexes of the invention are prepared in a conventional manner, for example from complexes known from the state of the art, by ligand exchange, that is to say addition of the appropriate carbene of formula II.1 or II.2 to a metal complex of the metal M in solution, designated precursor complex.

Appropriate precursor complexes are the Karstedt complex of formula:

in which Vi represents the vinyl radical; and more generally

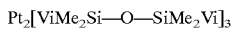

where M, $R_5$, $R_6$, $R_4$, $R_3$, $R_1$, $R_2$, $Y_1$, X and $Y_2$ are as defined above, such as for example

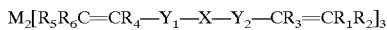, it being understood that M, $R_1$, $R_2$, $R_3$, $R_4$, $R_5$, $R_6$, $R_d$ and $R_e$ are as defined above;

$Pt(COD)_2$ in which COD represents cyclooctadiene and more generally $M(COD)_2$ where M is a group 8 metal; or alternatively metal complexes of olefin and of bisphosphine.

The complexes of formula I are generally prepared from precursor complexes having, as ligand, at least one diolefin compound of formula III:

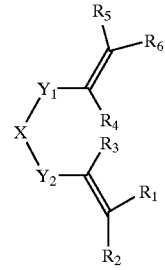

III in which $R_1$, $R_2$, $R_3$, $R_4$, $R_5$, $R_6$, X, $Y_1$ and $Y_2$ are as defined above for formula I.

These ligands are either commercially available, or are easily prepared by a person skilled in the art from commercial compounds.

When X represents $NR_a$ and $Y_1$ and $Y_2$, independently of each other, represent $CR_bR_c$, the compounds of formula III are amines which can be easily prepared using conventional organic chemistry methods. Thus, when $R_a$ is different from a hydrogen atom, these amines may be easily prepared from the corresponding primary amine of formula $R_aNH_2$ by the action of appropriate chlorides, preferably in the presence of an organic or inorganic base.

When the diolefin III is symmetric (that is to say that $R_4$=$R_3$; $R_5$=$R_2$; $R_1$=$R_6$; and $Y_1$=$Y_2$), $R_aNH_2$ is reacted with two equivalents of a chloride of formula:

Cl—$CR_bR_c$—$CR_3$=$CR_1R_2$ (IV)

in the presence of a base.

When the diolefin III is disymmetric, it is preferable to protect the amino group of $R_aNH_2$ with an appropriate conventional protecting group P before reacting the resulting compound of formula $R_aNHP$ with the chloride of formula V:

Cl—$CR_b^2R_c^2$—$CR_3$=$CR_1R_2$ (V)

in the presence of an appropriate base.

Then, after deprotection, the resulting amine is reacted with a chloride of formula:

Cl—$CR_b^1R_c^1$—$CR_4$=$CR_5R_6$ (VI)

in order to obtain the expected amine.

In the formulae IV, V and VI above, the substituents $R_1$, $R_2$, $R_3$, $R_4$, $R_5$ and $R_6$ are as defined for formula I; $R_b^1$ and $R_b^2$ are as defined for $R_b$; and $R_c^1$ and $R_c^2$ are as defined for $R_c$.

The groups P for protecting the amine functional groups as well as the corresponding methods of deprotection are described in Protective Groups in Organic Synthesis, Greene T. W. and Wuts P. G. M., ed. John Wiley and Sons, 1991, and in Protecting Groups, Kocienski P. J., 1994, Georg Thieme Verlag.

When $R_a$ represents a hydrogen atom, it is desirable to select, as starting compound, the amine having the following formula VII, protected beforehand on the amino functional group by a protecting group P as defined above:

$$NH_2-CR_b^2R_c^2-CR_3=CR_1R_2 \quad (VII).$$

The protected amine VII is reacted with a chloride of formula VI as defined above, preferably in the presence of a base, and then, upon deprotection of the amino functional group, the expected compound of formula III is isolated.

Appropriate bases are for example an organic base chosen from triethylamine, diisopropylamine, pyridine and N,N-dimethylaniline or an inorganic base such as NaOH, KOH, NaHCO$_3$, Na$_2$CO$_3$, KHCO$_3$ and K$_2$CO$_3$.

When X represents O and Y represents CR$_b$R$_c$, the compounds of formula III are ethers. These ethers are commercially available or are prepared in a manner known per se from commercially available compounds.

The compounds of formula III in which X represents CR$_f$R$_g$ and Y represents CR$_b$R$_c$ are diolefins which are easily accessible to a person skilled in the art by synthesis or are commercially available.

The compounds of formula III in which X represents NR$_a$ where R$_a$ represents H or alkyl; R$_1$=R$_6$; R$_2$=R$_5$; R$_3$=R$_4$; and Y$_1$=Y$_2$=SiR$_d$R$_e$ may be prepared by the action of an amine R$_a$—NH$_2$ with two equivalents of a silyl chloride of formula:

$$ClSiR_dR_e-CR_3=CR_1R_2$$

in which R$_e$, R$_d$, R$_1$, R$_2$ and R$_3$ are as defined above.

The compounds of formula III in which X represents NR$_a$, R$_a$ being as defined above in formula I; Y$_1$=Y$_2$=SiR$_d$R$_e$ where R$_e$ is as defined above in formula I; the two groups R$_d$ together form the chain:

$$-NR_a-(SiR_eR_d^0-NR_a)_n-$$

in which R$_a$ and R$_e$ are as defined above; n represents an integer from 1 to 3; R$_d^0$ represents —CR$_3$=CR$_1$R$_2$; R$_1$=R$_6$; R$_2$=R$_5$ and R$_3$=R$_4$, may be prepared by reacting the amine R$_a$—NH$_2$ with the silyl chloride of formula:

$$Cl_2SiR_e-CR_3=CR_1R_2$$

in which R$_e$, R$_1$, R$_2$ and R$_3$ are as defined above.

The compounds of formula III in which X represents O, and Y$_1$ and Y$_2$ represent SiR$_d$R$_e$ are linear, branched or cyclic siloxanes which are commercially available or whose preparation is possible from commercial compounds, using conventional state of the art methods. Examples of preferred siloxanes of formula III are ViMe$_2$SiOSiMe$_2$Vi and (MeViSiO)$_3$, the second formula representing a cyclosiloxane in which Vi represents vinyl.

In the case of the symmetric compounds of formula III, that is to say those for which R$_1$=R$_6$; R$_2$=R$_5$; R$_3$=R$_4$ and Y$_1$=Y$_2$, one of the variants of following synthesis may be used.

(Variant a): For the preparation of said symmetric siloxanes of formula III for which R$_1$, R$_2$, R$_3$, R$_d$ and R$_e$ are independently chosen from alkyl, aryl, alkenyl and alkynyl, a silyl chloride of formula Cl$_2$SiR$_d$R$_e$ may be reacted with an organometallic compound of formula:

$$CR_1R_2=CR_3-Mg-Hal$$

where R$_1$, R$_2$, R$_3$ are as defined above and Hal represents a halogen atom under the usual reaction conditions using magnesium compounds.

(Variant b): For the preparation of said symmetric siloxanes of formula III for which R$_1$=R$_2$=R$_3$=H and R$_c$, R$_d$ are chosen from alkenyl, alkynyl, aryl and alkyl, a silyl chloride of formula Cl$_2$SiR$_d$—CH=CH$_2$ may be reacted with an organometallic compound of formula:

$$Re-Mg-hal$$

in which R$_e$ is as defined above and hal represents halogen.

For the use of this variant, persons skilled in the art may refer to J. Gen. Chem., USSR, 1977, 47, 1402–1406.

(Variant c): For the preparation of said symmetric siloxanes of formula III in which R$_1$=R$_3$=H and R$_2$ represents alkyl, a siloxane of formula:

$$H-SiR_dR_e-O-SiR_dR_eH$$

can be reacted with two equivalents of an acetylene hydrocarbon of formula H—C≡C—R$_2$ in which R$_2$ is as defined above.

Cyclic siloxanes of formula III are described in U.S. Pat. No. 4,593,084.

The compounds of formula III in which X represents CR$_f$R$_g$ and Y$_1$ and Y$_2$ independently represent —SiR$_d$R$_e$ may be prepared using a method similar to one of those described in:

J. of Organometallic Chemistry, 1996, vol. 521, 99–107 (which method is more particularly appropriate for the preparation of the symmetric compounds of formula III in which Y$_1$=Y$_2$; R$_f$=R$_g$=H; R$_d$, R$_e$ represent alkyl or aryl optionally substituted with alkyl; R$_3$ represents a hydrogen atom; alkyl; or aryl which is optionally substituted; and R$_1$, R$_2$ are chosen from a hydrogen atom and alkyl);

J. of Organometallic Chemistry, 1997, vol. 545–546, 185–189 (which method is more particularly appropriate for the preparation of symmetric compounds of formula III in which Y$_1$=Y$_2$; R$_f$=R$_g$=Cl or Br; R$_d$ and R$_e$ represent alkyl; R$_1$=R$_2$=R$_3$=a hydrogen atom);

J. Chem. Soc., Perkin Trans II, 1987, p.381 (which method is more particularly appropriate for the preparation of the symmetric compounds of formula III in which Y$_1$=Y$_2$; R$_f$=R$_g$=SiG$_1$G$_2$G$_3$; R$_d$ and R$_e$ represent alkyl; R$_1$=R$_2$=R$_3$=a hydrogen atom).

The carbenes of formula II.1 and II.2 may be prepared by deprotonation of imidazolium salts, of tetrazolium salts, of triazolium salts or of pyrazolium salts according to the case, under the action of a base.

These reactions may be schematically represented as follows:

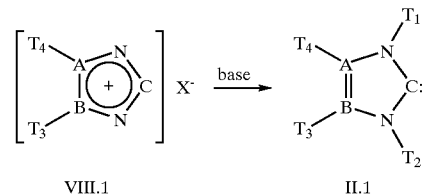

VIII.1      II.1

VIII.2

$$\left[\begin{array}{c} T_4 \diagdown_A\text{---}B\diagdown_C \\ T_2\diagup^N\diagdown_N\diagup \\ T_1 \end{array}\right] X^- \xrightarrow{\text{base}} \begin{array}{c} T_4\diagdown_A\text{=}B\diagdown_C: \\ T_2\diagup^N\diagdown_N\diagup \\ T_1 \end{array}$$

II.2

In these reaction schemes, $T_1$, $T_2$, $T_3$, $T_4$, A and B are as defined above for formula I and $X^-$ represents an anion.

The nature of the anion $X^-$ is not critical according to the invention. The anion $X^-$ is the anion derived from an organic or inorganic Brønsted acid (protic acid). Usually, the anion $X^-$ is derived from an acid having a pKa of less than 6. Preferably, $X^-$ is derived from an acid having a pKa of less than 4, even better of less than 2. The pKa values in question here are the pKa values for acids as measured in water.

Examples of acids are carboxylic acids of formula $G_o$—COOH in which $G_o$ represents alkyl, and for example $(C_1-C_{22})$alkyl; or alternatively aryl, and for example $(C_6-C_{18})$aryl optionally substituted with one or more alkyls, preferably one or more $(C_1-C_6)$alkyl; the sulfonic acids of formula $G_o$—SO$_3$H in which $G_o$ is as defined above; and the phosphonic acids of formula $G_o$—PO$_3$H in which $G_o$ is as defined above; other acids are HF, HCl, HBr, HI, $H_2SO_4$, $H_3PO_4$ and HClO$_4$.

Preferred examples of carboxylic acids are acetic acid, benzoic acid and stearic acid. By way of preferred sulfonic acid, there will be mentioned benzenesulfonic acid and by way of preferred phosphonic acid, there will be mentioned phenylphosphonic acid.

According to the invention, the anions $X^-$ derived from HF, HCl, HBr, HI, $H_2SO_4$ and $H_3PO_4$ acids are more particularly preferred.

Thus, particularly preferred anions $X^-$, according to the invention, are halide, sulphate, hydrogen sulphate, phosphate, hydrogen phosphate and dihydrogen phosphate anions. There may also be mentioned, as anions, tetrafluoroborates and hexaphenyl phosphate.

The bases which may be used for the deprotonation of the salts of formulae VIII.1 and VIII.2 are strong bases chosen from alkali metal hydrides, alkali metal hydroxides, alkali metal carboxylates, alkali metal alcoholates and alkali metal amides.

Examples of an appropriate base are therefore sodium hydride, potassium hydroxide, sodium methoxide, potassium tert-butoxide, lithium diisopropylamide and mixtures thereof.

The deprotonation reaction is preferably carried out in a solvent capable of dissolving the starting salt of formula VIII.1 or VIII.2, as well as the other reagents.

The nature of the solvent also depends on the strength of the base. Specifically in the case of a strong base and of particularly reactive starting salts, it may be necessary to carry out the procedure at low temperature.

Generally, the reaction temperature is between 40° C. and −78° C., preferably between 30 and −50° C., even better between 25 and −40° C., for example between 20 and −30° C.

Solvents which can be used in the method for preparing carbenes are cyclic or noncyclic ethers such as diethyl ether, diisopropyl ether, tetrahydrofuran, dioxane, dimethoxyethane or dimethyl ether of diethylene glycol.

Other solvents which can be used are dimethyl sulfoxide, dimethylformamide, dimethylacetamide, hexamethylphosphorylamide: [(CH$_3$)$_2$N]$_3$PO and hexamethylphosphoramide [(CH$_3$)$_2$N]$_3$P.

The carbenes of formula II.1 in which A and B both represent a carbon atom may also be prepared by reducing the corresponding thiones of formula IX:

$$\begin{array}{c} T_4\diagdown_A\diagdown_N\diagup^{T_1} \\ \| \quad\quad C\text{=}S \\ T_3\diagup^B\diagdown_N \\ T_2 \end{array} \xrightarrow{\underset{\Delta}{K}} \begin{array}{c} T_4\diagdown_A\diagdown_N\diagup^{T_1} \\ \| \quad\quad C: \\ T_3\diagup^B\diagdown_N \\ T_2 \end{array}$$

IX

This reaction was described by N. Kuhn in Synthesis, 1993, 561. Preferably, the reduction is carried out in an ether or amide type solvent, as defined above, at a temperature of between 50 and 150° C., in the presence of potassium.

The starting salts of formula VIII.1 and VIII.2 may, for their part, prepared by reacting the corresponding imidazoles, pyrazoles, triazoles and tetrazoles with an appropriate acid.

The nature of the anion $X^-$ in the salts of formula VIII.1 and VIII.2 depends on the acid used at this stage. The acids which can be used are for example those listed above and from which $X^-$ is derived.

Another method for synthesizing the salts of formula VIII.1 in which A=B=C is described in U.S. Pat. No. 5,077,414.

This method comprises the reaction of an α-dicarbonyl compound X of formula:

$$T_4\text{---}\underset{\underset{O}{\|}}{C}\text{---}\underset{\underset{O}{\|}}{C}\text{---}T_3$$

X in which $T_3$ and $T_4$ are as defined above with HCHO and two amines of formulae $T_1$—NH$_2$ and $T_2$—NH$_2$ in the presence of an appropriate acid.

Other methods for preparing the salts of formulae VIII.1 and VIII.2 are proposed in Chem. Eur. J. 1996, 2, No. 12, pages 1627–1636 and Angew. Chem. Int. Ed. Engl. 1997, 36, 2162–2187.

The compounds of formula IX may be prepared by condensing an appropriate thiourea of formula XI:

$$T_1HN\text{---}\underset{\underset{\|}{S}}{C}\text{---}NHT_2$$

XI with an α-hydroxyketone of formula XII:

$$\begin{array}{c} HO\diagdown\quad\quad O \\ \quad CH\text{---}C\diagup^{\|} \\ T_3\diagup\quad\quad\diagdown T_4 \end{array}$$

XII in which $T_1$, $T_2$, $T_3$ and $T_4$ are as defined above. Appropriate operating conditions are in particular described by N. Kuhn in Synthesis, 1993, 561.

According to a particularly preferred embodiment of the invention, the metal complex of the invention has the formula:

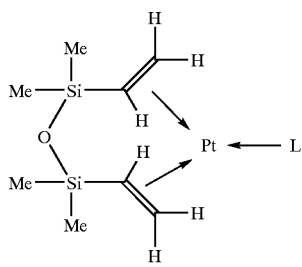

in which L is as defined above.

A simple method for preparing this complex consists in reacting the carbene L with the Karstedt catalyst having the average formula Pt$_2$[ViMe$_2$Si—O—SiMe$_2$Vi]$_3$ in which Vi represents the vinyl radical.

This reaction may be carried out in bulk or in a solvent.

Examples of appropriate solvents are cyclic or noncyclic ethers such as diethyl ether, diisopropyl ether, tetrahydrofuran, dioxane, dimethoxyethane or dimethyl ether of diethylene glycol; amides such as dimethylformamide, or dimethylacetamide; aromatic hydrocarbons (such as toluene, xylenes and more particularly toluene); and aliphatic alcohols of the (C$_1$–C$_4$)alkanol type (such as ethanol or isopropanol).

Advantageously, the reaction is carried out in an ether, and preferably in tetrahydrofuran.

The reaction temperature usually varies between 10 and 50° C., preferably between 15 and 35° C., very preferably between 20 and 25° C.

It is desirable to carry out the procedure in the presence of a slight excess of carbene relative to the platinum. Thus, the molar ratio of the carbene L to the platinum generally varies between 1 and 1.3, preferably between 1 and 1.1.

A simple way of proceeding consists in pouring, at the appropriate temperature, a carbene solution in a solvent, into a reactor containing a solution of the Karstedt catalyst in this same solvent.

The molarity of the solutions of the carbene and of the catalyst is not critical according to the invention.

According to another of its aspects, the invention relates to a catalytic composition comprising, as active substance, one or more metal complexes according to the invention.

The complexes of formula I of the invention can be used as catalysts for the hydrosilylation reactions. The catalysts of the invention allow homogeneous catalysis of the reaction.

The expression hydrosilylation reaction is understood to mean, according to the invention, the reaction of a compound having an ethylene double bond or having an acetylene triple bond (unsaturated compound) with a compound having at least one unit

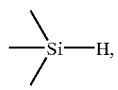

in order to form a C—Si bond.

The hydrosilylation reaction may be schematically represented as follows, in the case of a compound having an ethylene double bond:

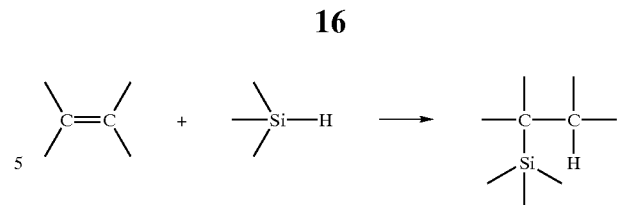

and, in the case of a compound having an acetylene triple bond:

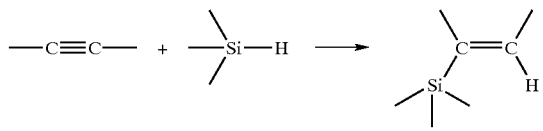

The compounds having an ethylene double bond may comprise one or more double bonds and from 2 to 40 carbon atoms. These compounds may be aliphatic hydrocarbons having a linear or branched hydrocarbon chain, or alternatively cyclic hydrocarbons, said cyclic or aliphatic hydrocarbons optionally carrying one or more substituents of (C$_6$–C$_{18}$)aryl type optionally substituted with (C$_1$–C$_6$)alkyl. The double bonds are generally terminal. Preferably, the compound having an ethylene double bond has a single double bond.

Examples of olefins are ethylene, propylene, 1-butylene, 1-pentene, 2-methyl-1-butene, 1-hexene, 1-heptene, 1-octene, 3-ethyl-1-hexene, 1-decene, 4,4-dimethyl-1-nonene, vinylcyclohexene, styrene and 2-vinylnaphthalene.

The compounds having an acetylene triple bond may comprise one or more triple bonds and from 2 to 40 carbon atoms. These compounds are generally aliphatic hydrocarbons having a linear or branched hydrocarbon chain, optionally substituted with (C$_3$–C$_{10}$)cycloalkyl (which cycloalkyl may optionally carry one or more (C$_1$–C$_6$)alkyl) and/or with (C$_6$–C$_{10}$)aryl (which aryl may optionally carry one or more (C$_1$–C$_6$)alkyl). Preferably, the compounds containing an acetylene triple bond have a single triple bond. The triple bonds are generally terminal. Examples thereof are: ethynyl, 2-propynyl, 1-propynyl and 2-penten-4-ynyl.

The hydrosilylation of compounds having both one or more ethylene double bonds and one or more acetylene triple bonds can also be envisaged in the context of the invention.

Under the operating conditions normally prescribed in the literature for hydrosilylation reactions, the formation of two types of by-products of the hydrosilylation reaction are observed, namely the products of isomerization and the products of hydrogenation. The products of isomerization result from the isomerization of double bonds. The products of hydrogenation result from the hydrogenation of double and triple bonds.

Surprisingly, when the hydrosilylation is carried out using the metal complexes of the invention as catalyst, the formation of these by-products is greatly limited. More particularly, a high reduction in the level of isomers formed is observed.

The hydrosilylation reaction may be carried out in a solvent or in the absence of solvent. As a variant, one of the reagents can play the role of solvent: for example the compound having an ethylene double bond or having an acetylene triple bond.

Appropriate solvents are solvents which are miscible with the compound containing an Si—H unit.

Under the hydrosilylation reaction conditions, the catalyst complex of the invention should be solubilized in the reaction medium.

According to a preferred embodiment of the invention, the reaction medium for the reaction for preparing the catalyst complex is used as it is or after dilution, without intermediate isolation.

The compound containing an Si—H unit may be a silicon hydride of formula XIII:

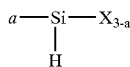

XIII in which:

X is a radical comprising a heteroatom such as O, Si, a halogen atom or the carbon atom of an aliphatic or aromatic group;

R is a hydrogen atom, an alkyl group, an aryl group, a cycloalkyl group, an alkoxy group, an aryloxy group or a cycloalkoxy group;

a is an integer from 0 to 3.

It should be understood that, according to the invention, the aliphatic, aromatic, alkyl, aryl, cycloalkyl, alkoxy, aryloxy or cycloalkoxy groups may be substituted or otherwise. The nature of the substituents is defined so as not to give rise to side reactions during the hydrosilylation reaction.

Appropriate examples of silane are $HSi(OC_2H_5)_3$ and $HSi(C_2H_5)_3$.

The compound containing an Si—H unit may be a siloxane of formula XIV:

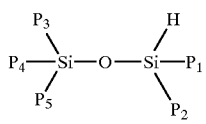

XIV in which $P_1$ to $P_5$ are independently chosen from alkyl, aryl, alkoxy, aryloxy, arylalkyl or arylalkoxy which are optionally substituted, it being possible for $P_3$, $P_4$ and/or $P_5$ to also represent a hydrogen atom.

Preferably, $P_1$ to $P_5$ are independently chosen from a $(C_1-C_{22})$alkyl, preferably $(C_1-C_{10})$alkyl, group; a $(C_6-C_{10})$ aryl group optionally substituted with one or more $(C_1-C_{10})$ alkyl and/or $(C_1-C_{10})$alkoxy; a $(C_1-C_{22})$alkoxy, preferably $(C_1-C_{10})$alkoxy, group; a $(C_6-C_{10})$aryloxy group in which the aryl portion is optionally substituted with $(C_1-C_6)$alkyl and/or $(C_1-C_6)$alkoxy; a $(C_6-C_{10})$aryl$(C_1-C_{10})$alkyl group in which the aryl portion is optionally substituted with $(C_1-C_6)$alkyl and/or $(C_1-C_6)$alkoxy; or alternatively a $(C_6-C_{10})$aryl-$(C_1-C_{10})$alkoxy group in which the aryl portion is optionally substituted with $(C_1-C_6)$alkyl and/or $(C_1-C_6)$alkoxy.

The compound having an Si—H unit may be a polymer of polyhydrogen siloxane type. Other appropriate polymers and copolymers are the polyhydrosilanes comprising a large number of recurring units containing Si—H bonds.

Preferably, the polymers which can be used have recurring units of formula:

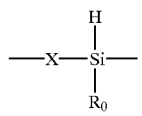

in which X is a radical comprising a heteroatom such as O, Si or the carbon atom of an aliphatic or aromatic group; and $R_0$ is a hydrogen atom or an organic group chosen from alkyl, aryl, cycloalkyl, alkoxy, aryloxy or cycloalkoxy. By way of examples, there may be mentioned the polyhydrosiloxanes of formula:

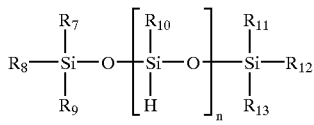

in which $R_7$ to $R_{13}$ are independently a hydrogen atom or an organic group. Preferably, $R_7$, $R_5$, $R_9$, $R_{10}$, $R_{11}$, $R_{12}$ and $R_{13}$ are chosen from a hydrogen atom, an alkyl, aryl, cycloalkyl, alkoxy, aryloxy and cycloalkoxy group;

n is an integer at least equal to 1 and preferably at least equal to 10 and, even better, between 10 and 100.

Appropriate polymers are polymethyl hydrogen siloxane, polydimethylsiloxane having a terminal —SiH group, methyl hydrogen dimethylsiloxane copolymers, methyl hydrogen methyloctylsiloxane copolymers and methyl hydrogen cyclosiloxane polymers.

In general, the polymers which can be used in the reaction have a mean molecular mass of 300 or more and preferably of between 300 and 10,000 (g/mol).

Examples of silicon hydrides are described in U.S. Pat. No. 5,359,113.

Examples of solvents which can be used for the hydrosilylation are in particular the aliphatic hydrocarbons (such as pentane, hexane, heptane, pentamethylheptane or the fractions from the distillation of petroleum); aromatic hydrocarbons (such as benzene, toluene and xylenes: ortho-xylene, para-xylene and meta-xylene); halogenated aliphatic or aromatic hydrocarbons (such as tetrachloroethylene); or ethers (such as tetrahydrofuran or dioxane).

The hydrosilylation reaction may be carried out at a temperature of between 15° C. and 300° C., for example between 20 and 240° C., even better between 70 and 200° C., in particular between 50 and 140° C., most preferably between 50 and 100° C.

The relative quantity of unsaturated compound and of compound containing an Si—H unit may be controlled so as to ensure the reaction of all the unsaturations with Si—H bonds.

It is nevertheless preferable to carry out the procedure in the presence of a molar excess of unsaturation.

The molar ratio of the unsaturations to the Si—H bonds generally varies between 1:100 and 10:1.

The concentration of unsaturated compound in the reaction medium is between 2 and 50% by weight.

According to the invention, the hydrosilylation reaction is carried out in the presence of a catalytic quantity of one or more complexes according to the invention. The expression catalytic quantity is understood to mean less than one molar equivalent of platinum relative to the quantity of unsaturations present in the reaction medium.

In general, it is sufficient to introduce into the reaction medium less than 1000 ppm, preferably less than 100 ppm, even better less than 50 ppm of platinum calculated relative to the total mass of the unsaturated compound and of the compound containing Si—H units.

According to a preferred embodiment of the invention, the unsaturated compound, the catalyst and the solvent are placed, with stirring, in a reactor. The whole is heated to the desired temperature and the compound containing the unit

is introduced, with stirring.

The invention is illustrated in the text which follows in the light of the following examples.

EXAMPLE 1

1—Preparation of the Carbene of Formula

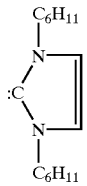

(cf. Chem. Eur. J. 1996, 2, 1627).

For this reaction, all the glassware used is dried in an oven at 150° C. overnight and then cooled under argon.

The THF is distilled over sodium/benzophenone just before use.

A 100 ml three-necked flask is loaded with 2.70 g (10 mmol) of 1,3-dicyclohexylimidazolinium chloride and then purged with an argon stream before being suspended in 20 ml of THF. About 50 ml of ammonia are then condensed at 78° C. in the three-necked flask, causing partial dissolution of the salt. The acetone/dry ice bath is removed and 270 mg of NaH at 95% (10.7 mmol-1.07 eq.) are slowly added using a solid-charging vessel. Each addition of NaH is followed by a high gaseous emission ($H_2$) and the salt in suspension gradually dissolves. The reaction mixture is stirred for 1 h 30 min at the reflux temperature of the solvent. The ammonia is then evaporated and a pale yellow solution is obtained as well as a solid in suspension (NaCl). This solution, whose carbene concentration is 0.5M in THF, is used immediately for the preparation of the complexes.

2—Preparation of the Platinum Complex of Formula

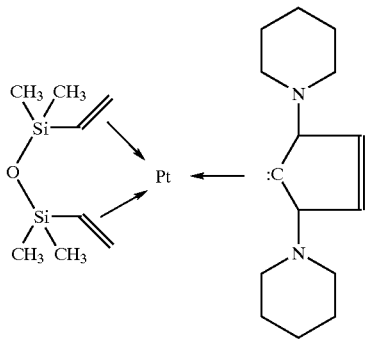

A Karstedt solution containing 10% by weight of platinum (that is 1.52 mmol of platinum) is prepared in accordance with the procedure described in U.S. Pat. No. 3,775,452.

To 3 g of this solution, kept stirred and diluted in 10 ml of tetrahydrofuran there are added dropwise, using a dropping funnel, 3.2 ml of a 0.5M solution of the carbene of formula:

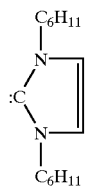

in tetrahydrofuran. The addition is complete after 10 minutes. The reaction mixture is then stirred for 50 minutes at room temperature. Where appropriate, the light insoluble material is filtered and the reaction mixture is concentrated under vacuum.

After concentration, a slightly yellow viscous residue is obtained. Within a few hours, an abundant white solid precipitates from the residual divinyltetramethyldisiloxane. It is filtered, washed with a few milliliters of hexamethyldisilazane, and then of pentane. 570 mg (60% yield) of an analytically pure white powder are thus obtained.

A fraction of this powder is recrystallized from a dichloromethane/absolute ethanol mixture. The resultant crystals are analyzed by X-ray diffraction. The analysis confirms the structure of the complex obtained.

EXAMPLE 2

1—Preparation of the Carbene of Formula

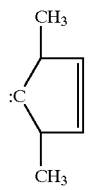

This carbene is prepared using the procedure illustrated in example 1, paragraph 1, except that the 2.7 g (10 mmol) of 1,3-dicyclohexylimidazolinium chloride are replaced by 2.3 g (10 mmol) of 1,3-dimethylimidazolinium iodide.

2—Preparation of the Platinum Complex of Formula

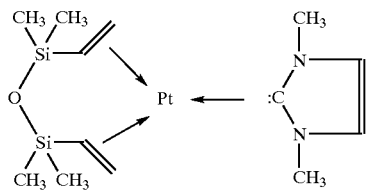

This complex is prepared using the procedure of example 1, except that the carbene used as starting material has the formula:

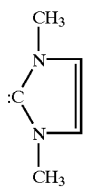

After concentration, a yellow paste is obtained. It is filtered and abundantly washed with hot pentane. A whitish solid is isolated (35% yield), which is recrystallized from ethanol. The resulting crystals are analyzed by X-ray diffraction. The analysis confirms the structure of the complex obtained.

EXAMPLE 3

Hydrosilylation of oct-1-ene by the Action of $(CH_3)_3Si$—O—$Si(CH_3)(H)$—$OSi(CH_3)_3$ 5 g (45 mmol) of oct-1-ene, 10 g (1 equivalent of SiH units relative to oct-1-ene) of $(CH_3)_3SiO$—$Si(CH_3)(H)$—$OSi(CH_3)_3$, 5 g of dodecane (used as internal standard for analysis by gas chromatography) and ortho-xylene in sufficient quantity so as to ensure a 0.5M concentration of silylated reagent and of oct-1-ene, are placed in a 250 ml three-necked reactor equipped with a condenser, with magnetic stirring and with a thermometric sheath, and heated using an oil bath. The whole is heated to 70° C. and kept stirred.

Next, a solution of the catalyst in dichloromethane containing 30 ppm of platinum calculated relative to the total quantity of silylated derivative and of oct-1-ene, is added to the preceding mixture, all at once.

The progress of the reaction is monitored by gas chromatography (GC).

The successive samples analyzed by GC are eluted beforehand on a column of activated charcoal.

The preceding hydrosilylation reaction is carried out under the same conditions starting with three different catalysts:

the Karstedt catalyst prepared according to U.S. Pat. No. 3,775,452;

the catalyst prepared in example 1;

the catalyst prepared in example 2.

The results obtained, expressed as rate of conversion (τ) of Si—H bonds in the silylated derivative and as percentage of isomerization (p) are reported in the following table.

TABLE

| Catalyst | τ (%) | p (%) |
|---|---|---|
| Karstedt | 80 | 17 |
| Example 1 | 82 | 4.5 |
| Example 2 | 85 | 3.7 |

It is observed that the catalysts of the invention lead to much lower percentages of isomerization (by a factor of 3).

EXAMPLE 4

In this example, the hydrosilylation of 1-octene is carried out by the action of $(CH_3)_3SiO$—$Si(H)(CH_3)$—$OSi(CH_3)_3$ in the presence of the complex of example 2 as catalyst.

The quantities of reagents and of catalyst brought into contact are the same as in example 3. Only the manner of proceeding was modified. 5 g (45 mmol) of oct-1-ene, 5 g of dodecane and the solution of the catalyst in dichloromethane (which contains 30 ppm of platinum calculated relative to the total quantity of silylated derivative and of oct-1-ene) are placed in a 100 ml three-necked flask equipped with magnetic stirring and a condenser, and heated using an oil bath. This solution is kept stirred and heated to 70° C. Next, 10 g (1 equivalent of Si—H units relative to oct-1-ene) of $(CH_3)_3SiO$—$Si(CH_3)(H)$—$OSi(CH_3)_3$ are introduced dropwise into the reaction medium. The progress of the reaction is monitored by gas chromatography. A rate of conversion of Si—H bonds in the silylated derivative of 96% and a percentage of isomerization of 1.5% are obtained.

What is claimed is:

1. A metal complex of formula I

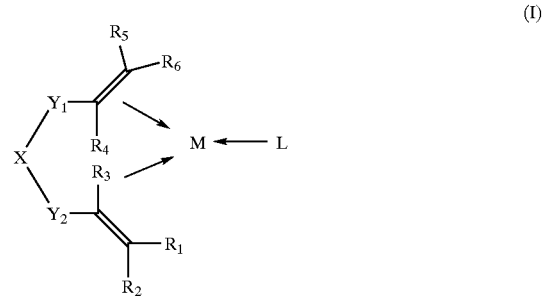

in which:

M represents a metal having an oxidation number 0 chosen from the group 8 metals in the Periodic Table as published in the Handbook of Chemistry and Physics, 65th Edition, 1984–1985;

X represents O, $NR_a$ or $CR_fR_g$;

$Y_1$ and $Y_2$ represent, independently of each other, $CR_bR_c$ or $SiR_dR_e$;

$R_1$, $R_w$, $R_5$ and $R_6$, which are identical or different, are chosen from a hydrogen atom, an alkyl group and an aryl group optionally substituted with alkyl;

$R_3$, $R_4$, $R_a$, $R_b$, $R_c$ are independently chosen from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_d$ and $R_e$ are independently chosen from alkenyl; alkynyl; alkyl; alkoxy; acyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two $R_d$ groups linked to two separate silicon atoms together form a chain of formula:

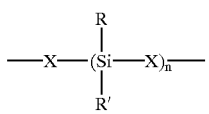

in which n is an integer from 1 to 3; X is as defined above; R and R', which are identical or different, take any one of the meanings given above for $R_e$, it being understood that when N is 2 or 3, a single silicon atom of said chain may be substituted with one or two alkenyl or alkynyl groups; or alternatively when $Y_1$ and $Y_2$ independently represent $SiR_dR_e$, two $R_d$ groups linked to separate silicon atoms together form a saturated hydrocarbon chain, the two $R_b$ groups together with said silicon atoms and X forming a 6- to 10-membered ring; or alternatively when $Y_1$ and $Y_2$ independently represent $CR_bR_c$, two $R_b$ groups linked to separate carbon atoms together form a saturated hydrocarbon chain, the two $R_b$ groups together with the carbon atoms carrying them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_wG_3$ where $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy;

L represents a carbene of formula II.1 or II.2:

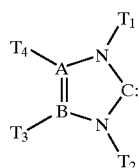

II.1

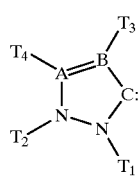

II.2 in which:

A and B independently represent C or N, it being understood that when A represents N, then $T_4$ represents nothing and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy;

$T_1$ and $T_2$ independently represent an alkyl group; an alkyl group which is perfluorinated or optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively the substituents $T_1$, $T_2$, $T_3$ and $T_4$, may form in pairs, when they are located on two adjacent summits in the formulae II.1 and II.2, a saturated or unsaturated hydrocarbon chain.

2. A metal complex of formula I

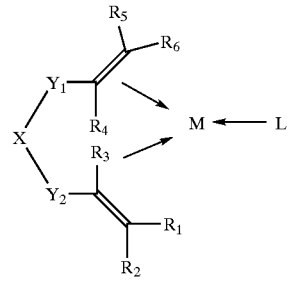

in which:

M represents a metal having an oxidation number 0 chosen from the group 8 metals in the Periodic Table as published in the Handbook of Chemistry and Physics, 65th Edition, 1984–1 985;

X represents O, $NR_a$ or $CR_fR_g$;

$Y_1$ and $Y_2$ represent, independently of each other, $CR_bR_c$ or $SiR_dR_e$;

$R_1$, $R_w$, $R_5$ and $R_6$, which are identical or different, are chosen from a hydrogen atom, an alkyl group and an aryl group optionally substituted with alkyl;

$R_3$, $R_4$, $R_a$, $R_b$, $R_c$ are independently chosen from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_d$ and $R_e$ are independently chosen from alkenyl; alkynyl; alkyl; alkoxy; acyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two $R_d$ groups linked to two separate silicon atoms together form a chain of formula:

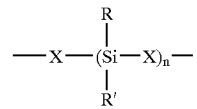

in which n is an integer from 1 to 3; X is as defined above; R and R', which are identical or different, take any one of the meanings given above for $R_e$, it being understood that when N is 2 or 3, a single silicon atom of said chain may be substituted with one or two alkenyl or alkynyl groups; or alternatively when $Y_1$ and $Y_2$ independently represent $SiR_dR_e$, two $R_d$ groups linked to separate silicon atoms together form a saturated hydrocarbon chain, the two $R_b$ groups together with said silicon atoms and X forming a 6- to 10-membered ring; or alternatively when $Y_1$ and $Y_2$ independently represent $CR_bR_c$, two $R_b$ groups linked to separate carbon atoms together form a saturated hydrocarbon chain, the two $R_b$ groups together with the carbon atoms carrying them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_wG_3$ where $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy;

L represents a carbene of formula II.1 or II.2:

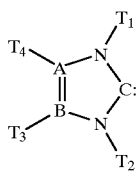

II.1

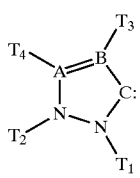

II.2 in which:

A and B independently represent C or N, it being understood that when A represents N, then $T_4$ represents nothing and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy;

$T_1$ and $T_2$ independently represent an alkyl group; an alkyl group which is perfluorinated or optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively the substituents $T_1$, $T_2$, $T_3$ and $T_4$, may form in pairs, when they are located on two adjacent summits in the formulae II.1 and II.2, a saturated or unsaturated hydrocarbon chain wherein X represents O; $Y_1$ and $Y_2$ represent, independently of each other, $SiR_dR_e$.

3. The metal complex as claimed in claim 1, in which L represents a carbene of formula II.1.

4. The metal complex as claimed in claim 1, wherein $R_1$, $R_2$, $R_5$ and $R_6$ are hydrogen atoms.

5. The metal complex as claimed in claim 1, wherein $R_3$ and $R_4$ represent a hydrogen atom; an alkyl group; an aryl group optionally substituted with alkyl; or a cycloalkyl group optionally substituted with alkyl.

6. A metal complex of formula I

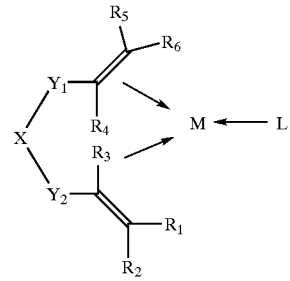

(I)

in which:

M represents a metal having an oxidation number 0 chosen from the group 8 metals in the Periodic Table as published in the Handbook of Chemistry and Physics, 65th Edition, 1984–1985;

X represents O, $NR_a$ or $CR_fR_g$;

$Y_1$ and $Y_2$ represent, independently of each other, $CR_bR_c$ or $SiR_dR_e$;

$R_1$, $R_w$, $R_5$ and $R_6$, which are identical or different, are chosen from a hydrogen atom, an alkyl group and an aryl group optionally substituted with alkyl;

$R_3$, $R_4$, $R_a$, $R_b$, $R_c$ are independently chosen from a hydrogen atom; an alkyl group; an acyl group; an aryl group optionally substituted with alkyl; a cycloalkyl group optionally substituted with alkyl; and an arylalkyl group in which the aryl portion is optionally substituted with a alkyl;

$R_d$ and $R_e$ are independently chosen from alkenyl; alkynyl; alkyl; alkoxy; acyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two $R_d$ groups linked to two separate silicon atoms together form a chain of formula:

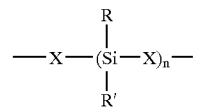

in which n is an integer from 1 to 3; X is as defined above; R and R', which are identical or different, take any one of the meanings given above for $R_e$, it being understood that when N is 2 or 3, a single silicon atom of said chain may be substituted with one or two alkenyl or alkynyl groups; or alternatively when $Y_1$ and $Y_2$ independently represent $SiR_dR_e$, two $R_d$ groups linked to separate silicon atoms together form a saturated hydrocarbon chain, the two $R_b$ groups together with said silicon atoms and X forming a 6- to 10-membered ring; or alternatively when $Y_1$ and $Y_2$ independently represent $CR_bR_c$, two $R_b$ groups linked to separate carbon atoms together form a saturated hydrocarbon chain, the two $R_b$ groups together with the carbon atoms carrying them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_wG_3$ where $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy;

L represents a carbene of formula II.1 or II.2:

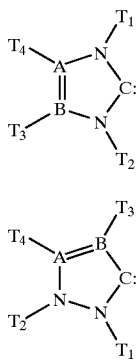

in which:

A and B independently represent C or N, it being understood that when A represents N, then $T_4$ represents nothing and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy;

$T_1$ and $T_2$ independently represent an alkyl group; an alkyl group which is perfluorinated or optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively the substituents $T_1$, $T_2$, $T_3$ and $T_4$, may form in pairs, when they are located on two adjacent summits in the formulae II.1 and II.2, a saturated or unsaturated hydrocarbon chain, wherein A and B both represent a carbon atom.

7. A metal complex of formula I

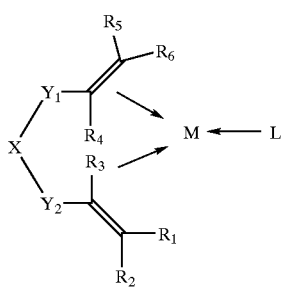

(I)

in which:

M represents a metal having an oxidation number 0 chosen from the group 8 metals in the Periodic Table as published in the Handbook of Chemistry and Physics, 65th Edition, 1984–1985;

X represents O, $NR_a$ or $CR_fR_g$;

$Y_1$ and $Y_2$ represent, independently of each other, $CR_bR_c$ or $SiR_dR_e$;

$R_1$, $R_w$, $R_5$ and $R_6$, which are identical or different, are chosen from a hydrogen atom, an alkyl group and an aryl group optionally substituted with alkyl;

$R_3$, $R_4$, $R_a$, $R_b$, $R_c$ are independently chosen from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_d$ and $R_e$ are independently chosen from alkenyl; alkynyl; alkyl; alkoxy; acyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two $R_d$ groups linked to two separate silicon atoms together form a chain of formula:

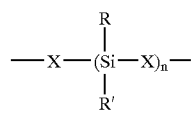

in which n is an integer from 1 to 3; X is as defined above; R and R', which are identical or different, take any one of the meanings given above for $R_e$, it being understood that when N is 2 or 3, a single silicon atom of said chain may be substituted with one or two alkenyl or alkynyl groups; or alternatively when $Y_1$ and $Y_2$ independently represent $SiR_dR_e$, two $R_d$ groups linked to separate silicon atoms together form a saturated hydrocarbon chain, the two $R_b$ groups together with said silicon atoms and X forming a 6- to 10-membered ring; or alternatively when $Y_1$ and $Y_2$ independently represent $CR_bR_c$, two $R_b$ groups linked to separate carbon atoms together form a saturated hydrocarbon chain, the two $R_b$ groups together with the carbon atoms carrying them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_wG_3$ where $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy;

L represents a carbene of formula II.1 or II.2:

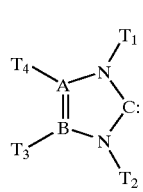

-continued

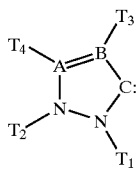

II.2 in which:

A and B independently represent C or N, it being understood that when A represents N, then $T_4$ represents nothing and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy;

$T_1$ and $T_2$ independently represent an alkyl group; an alkyl group which is perfluorinated or optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively the substituents $T_1$, $T_2$, $T_3$ and $T_4$, may form in pairs, when they are located on two adjacent summits in the formulae II.1 and II.2, a saturated or unsaturated hydrocarbon chain, wherein $T_3$ and $T_4$ represent a hydrogen atom.

8. A metal complex of formula I

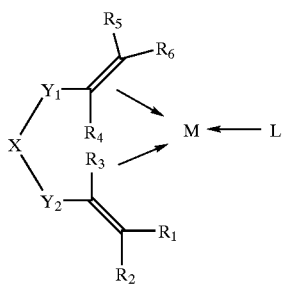

(I)

in which:

M represents a metal having an oxidation number 0 chosen from the group 8 metals in the Periodic Table as published in the Handbook of Chemistry and Physics, 65th Edition, 1984–1985;

X represents O, $NR_a$ or $CR_fR_g$;

$Y_1$ and $Y_2$ represent, independently of each other, $CR_bR_c$ or $SiR_dR_e$;

$R_1$, $R_w$, $R_5$ and $R_6$, which are identical or different, are chosen from a hydrogen atom, an alkyl group and an aryl group optionally substituted with alkyl;

$R_3$, $R_4$, $R_a$, $R_b$, $R_c$ are independently chosen from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_d$ and $R_e$ are independently chosen from alkenyl; alkynyl; alkyl; alkoxy; acyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two $R_d$ groups linked to two separate silicon atoms together form a chain of formula:

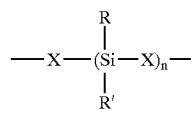

in which n is an integer from 1 to 3; X is as defined above; R and R', which are identical or different, take any one of the meanings given above for $R_e$, it being understood that when N is 2 or 3, a single silicon atom of said chain may be substituted with one or two alkenyl or alkynyl groups; or alternatively when $Y_1$ and $Y_2$ independently represent $SiR_dR_e$, two $R_d$ groups linked to separate silicon atoms together form a saturated hydrocarbon chain, the two $R_b$ groups together with said silicon atoms and X forming a 6-to 10-membered ring; or alternatively when $Y_1$ and $Y_2$ independently represent $CR_bR_c$, two $R_b$ groups linked to separate carbon atoms together form a saturated hydrocarbon chain, the two $R_b$ groups together with the carbon atoms carrying them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_wG_3$ where $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy;

L represents a carbene of formula II.1 or II.2:

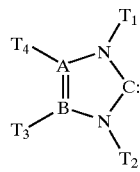

II.1

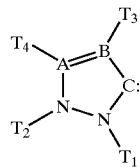

II.2 in which:

A and B independently represent C or N, it being understood that when A represents N, then $T_4$ represents nothing and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy;

$T_1$ and $T_2$ independently represent an alkyl group; an alkyl group which is perfluorinated or optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively the substituents $T_1$, $T_2$, $T_3$ and $T_4$, may form in pairs, when they are located on two adjacent summits in the formulae II.1 and II.2, a saturated or unsaturated hydrocarbon chain, wherein $T_1$ and $T_2$, which are identical or different, represent $(C_1-C_8)$alkyl or $(C_3-C_8)$cycloalkyl; or alternatively $R_3$ and $R_4$, which are identical or different, represent $(C_1-C_8)$alkyl or $(C_3-C_8)$cycloalkyl; or still alternatively $T_1$, $T_2$, $R_3$ and $R_4$, which are identical or different, represent $(C_1-C_8)$alkyl or $(C_3-C_8)$cycloalkyl.

9. A metal complex of formula I

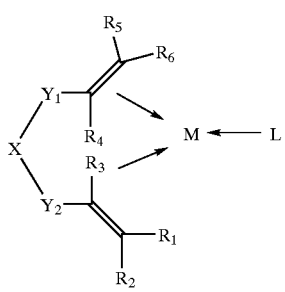

(I)

in which:

M represents a metal having an oxidation number 0 chosen from the group 8 metals in the Periodic Table as published in the Handbook of Chemistry and Physics, 65th Edition, 1984–1985;

X represents O, $NR_a$ or $CR_fR_g$;

$Y_1$ and $Y_2$ represent, independently of each other, $CR_bR_c$ or $SiR_dR_e$;

$R_1$, $R_w$, $R_5$ and $R_6$, which are identical or different, are chosen from a hydrogen atom, an alkyl group and an aryl group optionally substituted with alkyl;

$R_3$, $R_4$, $R_a$, $R_b$, $R_c$ are independently chosen from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_d$ and $R_e$ are independently chosen from alkenyl; alkynyl; alkyl; alkoxy; acyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two $R_d$ groups linked to two separate silicon atoms together form a chain of formula:

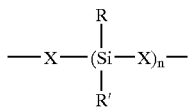

in which n is an integer from 1 to 3; X is as defined above; R and R', which are identical or different, take any one of the meanings given above for $R_e$, it being understood that when N is 2 or 3, a single silicon atom of said chain may be substituted with one or two alkenyl or alkynyl groups; or alternatively when $Y_1$ and $Y_2$ independently represent $SiR_dR_e$, two $R_d$ groups linked to separate silicon atoms together form a saturated hydrocarbon chain, the two $R_b$ groups together with said silicon atoms and X forming a 6- to 10-membered ring; or alternatively when $Y_1$ and $Y_2$ independently represent $CR_bR_c$, two $R_b$ groups linked to separate carbon atoms together form a saturated hydrocarbon chain, the two $R_b$ groups together with the carbon atoms carrying them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_wG_3$ where $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy;

L represents a carbene of formula II.1 or II.2:

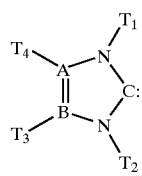

II.1

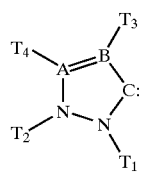

II.2 in which:

A and B independently represent C or N, it being understood that when A represents N, then $T_4$ represents nothing and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy;

$T_1$ and $T_2$ independently represent an alkyl group; an alkyl group which is perfluorinated or optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively the substituents $T_1$, $T_2$, $T_3$ and $T_4$, may form in pairs, when they are located on two adjacent summits in the formulae II.1 and II.2, a saturated or unsaturated hydrocarbon chain, wherein $T_1$ and $T_2$ are identical and represent $(C_3-C_8)$cycloalkyl.

10. A metal complex of formula I

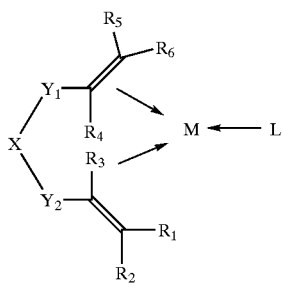
(I)

in which:

M represents a metal having an oxidation number 0 chosen from the group 8 metals in the Periodic Table as published in the Handbook of Chemistry and Physics, 65th Edition, 1984–1985;

X represents O, $NR_a$ or $CR_fR_g$;

$Y_1$ and $Y_2$ represent, independently of each other, $CR_bR_c$ or $SiR_dR_e$;

$R_1$, $R_w$, $R_5$ and $R_6$, which are identical or different, are chosen from a hydrogen atom, an alkyl group and an aryl group optionally substituted with alkyl;

$R_3$, $R_4$, $R_a$, $R_b$, $R_c$ are independently chosen from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_d$ and $R_e$ are independently chosen from alkenyl; alkynyl; alkyl; alkoxy; acyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two $R_d$ groups linked to two separate silicon atoms together form a chain of formula:

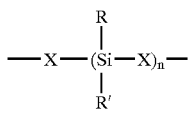

in which n is an integer from 1 to 3; X is as defined above; R and R', which are identical or different, take any one of the meanings given above for $R_e$, it being understood that when N is 2 or 3, a single silicon atom of said chain may be substituted with one or two alkenyl or alkynyl groups; or alternatively when $Y_1$ and $Y_2$ independently represent $SiR_dR_e$, two $R_d$ groups linked to separate silicon atoms together form a saturated hydrocarbon chain, the two $R_b$ groups together with said silicon atoms and X forming a 6- to 10-membered ring; or alternatively when $Y_1$ and $Y_2$ independently represent $CR_bR_c$, two $R_b$ groups linked to separate carbon atoms together form a saturated hydrocarbon chain, the two $R_b$ groups together with the carbon atoms carrying them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_wG_3$ where $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy;

L represents a carbene of formula II.1 or II.2:

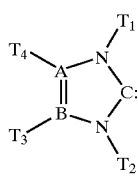
II.1

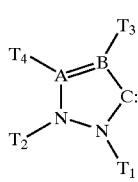
II.2 in which:

A and B independently represent C or N, it being understood that when A represents N, then $T_4$ represents nothing and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy;

$T_1$ and $T_2$ independently represent an alkyl group; an alkyl group which is perfluorinated or optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively the substituents $T_1$, $T_2$, $T_3$ and $T_4$, may form in pairs, when they are located on two adjacent summits in the formulae II.1 and II.2, a saturated or unsaturated hydrocarbon chain, wherein M is a metal selected from the group consisting of Pt, Pd and Ni.

11. A metal complex of formula I

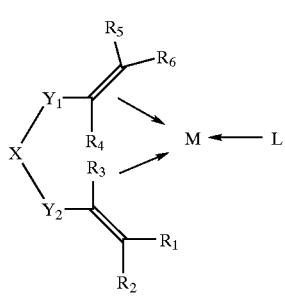
(I)

in which:

M represents a metal having an oxidation number 0 chosen from the group 8 metals in the Periodic Table as published in the Handbook of Chemistry and Physics, 65th Edition 1984–1985

X represents O, $NR_a$ or $CR_fR_g$;

$Y_1$ and $Y_2$ represent, independently of each other, $CR_bR_c$ or $SiR_dR_e$;

$R_1$, $R_w$, $R_5$ and $R_6$, which are identical or different, are chosen from a hydrogen atom, an alkyl group and an aryl group optionally substituted with alkyl;

$R_3$, $R_4$, $R_a$, $R_b$, $R_c$ are independently chosen from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_d$ and $R_e$ are independently chosen from alkenyl; alkynyl; alkyl; alkoxy; acyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two $R_d$ groups linked to two separate silicon atoms together form a chain of formula:

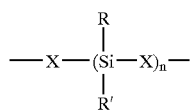

in which n is an integer from 1 to 3; X is as defined above; R and R', which are identical or different, take any one of the meanings given above for $R_e$, it being understood that when N is 2 or 3, a single silicon atom of said chain may be substituted with one or two alkenyl or alkynyl groups; or alternatively when $Y_1$ and $Y_2$ independently represent $SiR_dR_e$, two $R_d$ groups linked to separate silicon atoms together form a saturated hydrocarbon chain, the two $R_b$ groups together with said silicon atoms and X forming a 6- to 10-membered ring; or alternatively when $Y_1$ and $Y_2$ independently represent $CR_bR_c$, two $R_b$ groups linked to separate carbon atoms together form a saturated hydrocarbon chain, the two $R_b$ groups together with the carbon atoms carrying them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_wG_3$ where $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy;

L represents a carbene of formula II.1 or II.2:

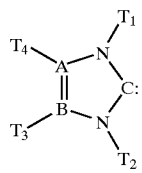

II.1

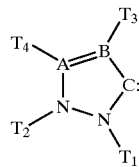

II.2 in which:

A and B independently represent C or N, it being understood that when A represents N, then $T_4$ represents nothing and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy;

$T_1$ and $T_2$ independently represent an alkyl group; an alkyl group which is perfluorinated or optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively the substituents $T_1$, $T_2$, $T_3$ and $T_4$, may form in pairs, when they are located on two adjacent summits in the formulae II.1 and II.2, a saturated or unsaturated hydrocarbon chain, wherein M is platinum having the oxidation number 0.

12. The metal complex as claimed in claim 1, wherein $R_3=R_4$; $R_1=R_6$; $R_2=R_5$; and either $Y_1=Y_2$, or $Y_1=CR_b^1R_c$ and $Y_2=CR_b^2R_c$ where $R_b^1$ and $R_b^2$ together form a symmetric chain, or alternatively $Y_1=SiR_d^1R_e$ and $Y_2=SiR_d^2R_e$ where $R_d^1$ and $R_d^2$ together form a symmetric chain.

13. A metal complex of formula I

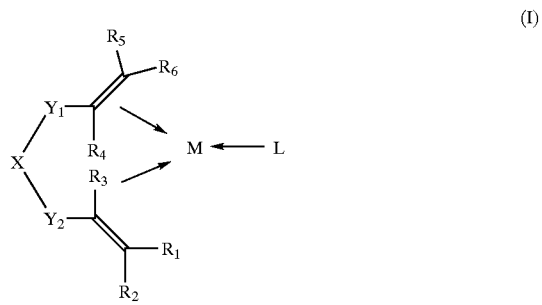

(I)

in which:

M represents a metal having an oxidation number 0 chosen from the group 8 metals in the Periodic Table as published in the Handbook of Chemistry and Physics, 65th Edition, 1984–1985;

X represents O, $NR_a$ or $CR_fR_g$;

$Y_1$ and $Y_2$ represent, independently of each other, $CR_bR_c$ or $SiR_dR_e$;

$R_1$, $R_w$, $R_5$ and $R_6$, which are identical or different, are chosen from a hydrogen atom, an alkyl group and an aryl group optionally substituted with alkyl;

$R_3$, $R_4$, $R_a$, $R_b$, $R_c$ are independently chosen from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_d$ and $R_e$ are independently chosen from alkenyl; alkynyl; alkyl; alkoxy; acyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two $R_d$ groups linked to two separate silicon atoms together form a chain of formula:

$$-X-(Si-X)_n-$$
with R and R' on the Si in which n is an integer from 1 to 3; X is as defined above; R and R', which are identical or different, take any one of the meanings given above for $R_e$, it being understood that when N is 2 or 3, a single silicon atom of said chain may be substituted with one or two alkenyl or alkynyl groups; or alternatively when $Y_1$ and $Y_2$ independently represent $SiR_dR_e$, two $R_d$ groups linked to separate silicon atoms together form a saturated hydrocarbon chain, the two $R_b$ groups together with said silicon atoms and X forming a 6- to 10-membered ring; or alternatively when $Y_1$ and $Y_2$ independently represent $CR_bR_c$, two $R_b$ groups linked to separate carbon atoms together form a saturated hydrocarbon chain, the two $R_b$ groups together with the carbon atoms carrying them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_wG_3$ where $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy;

L represents a carbene of formula II.1 or II.2:

II.1

II.2 in which:

A and B independently represent C or N, it being understood that when A represents N, then $T_4$ represents nothing and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy;

$T_1$ and $T_2$ independently represent an alkyl group; an alkyl group which is perfluorinated or optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively the substituents $T_1$, $T_2$, $T_3$ and $T_4$, may form in pairs, when they are located on two adjacent summits in the formulae II.1 and II.2, a saturated or unsaturated hydrocarbon chain, wherein the complex has the formula:

[structure diagram with Pt complex]

in which:

$R_3$ represents a hydrogen atom; a $(C_1-C_8)$alkyl group; or a $(C_3-C_8)$cycloalkyl group optionally substituted with $(C_1-C_4)$ alkyl;

$T_1$ and $T_2$ are identical and represent $(C_1-C_8)$ alkyl or $(C_3-C_8)$ cycloalkyl.

14. A method for the hydrosilylation of olefins or of acetylene derivatives, which is carried out in the presence of a catalyst comprising the metal complex of claim 1.

15. The hydrosilylation method as claimed in claim 14, comprising the reaction of an olefin with a siloxane having an Si—H unit.

16. A catalytic composition comprising, as active substance, one or more metal complexes as claimed in claim 1.

\* \* \* \* \*